(12) United States Patent
Anderson et al.

(10) Patent No.: US 6,916,480 B2
(45) Date of Patent: Jul. 12, 2005

US006916480B2

(54) WIPER CONTAINING A CONTROLLED-RELEASE ANTI-MICROBIAL AGENT

(75) Inventors: Ralph L. Anderson, Marietta, GA (US); Fred R. Radwanski, Stone Mountain, GA (US); James W. Clark, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 212 days.

(21) Appl. No.: 09/745,499

(22) Filed: Dec. 22, 2000

(65) Prior Publication Data

US 2002/0022050 A1 Feb. 21, 2002

Related U.S. Application Data

(60) Provisional application No. 60/173,400, filed on Dec. 28, 1999.

(51) Int. Cl.$^7$ .............................................. A01N 25/34

(52) U.S. Cl. ...................................... 424/404; 424/402

(58) Field of Search ................................. 424/402, 404

(56) References Cited

U.S. PATENT DOCUMENTS

| | | | |
|---|---|---|---|
| 2,449,274 A | 9/1948 | Broll ............................ 167/33 |
| 2,542,909 A | 2/1951 | De Wet ......................... 167/84 |
| 2,702,780 A | 2/1955 | Lerner .......................... 167/84 |
| 3,060,079 A | 10/1962 | Pattilloch ..................... 162/161 |
| 3,400,420 A | 9/1968 | Granville et al. ........ 15/104.93 |
| 3,640,841 A | 2/1972 | Winslow et al. ............ 162/164 |
| 3,663,262 A | 5/1972 | Cogan, Jr. .................. 117/62.1 |
| 3,704,096 A | 11/1972 | Verses et al. .............. 23/230 R |
| 3,857,934 A | 12/1974 | Bernstein et al. ............. 424/30 |
| 3,983,209 A | 9/1976 | Schmitt ........................ 424/78 |
| 4,045,364 A | 8/1977 | Richter ....................... 252/106 |
| 4,064,213 A | 12/1977 | Lazorisak et al. .......... 264/134 |
| 4,102,998 A | 7/1978 | Gutnick ....................... 424/115 |
| 4,125,659 A | 11/1978 | Klowak et al. .............. 428/153 |
| 4,188,447 A | 2/1980 | Ehlenz ........................ 428/310 |
| 4,205,043 A | 5/1980 | Esch et al. .................... 422/56 |
| 4,248,597 A | 2/1981 | McNeely .................. 23/230 R |
| 4,311,479 A | 1/1982 | Fenn et al. ..................... 8/495 |
| 4,323,557 A | 4/1982 | Rosso et al. ................... 424/28 |
| 4,343,788 A | 8/1982 | Mustacich et al. ............. 424/78 |
| 4,404,196 A | 9/1983 | Daudt et al. ................. 424/184 |
| 4,424,060 A | 1/1984 | Nakamura et al. ........... 8/115.5 |
| 4,436,780 A | 3/1984 | Hotchkiss et al. .......... 428/198 |
| 4,443,222 A | 4/1984 | Morris et al. ................... 8/189 |
| 4,454,110 A | 6/1984 | Caslavsky et al. ............. 424/54 |
| 4,496,322 A | 1/1985 | Sandham et al. ............ 433/217 |
| 4,504,442 A | 3/1985 | Rosenblatt et al. ............ 422/37 |
| 4,515,703 A | 5/1985 | Haq ............................. 252/92 |
| 4,533,435 A | 8/1985 | Intili ........................... 162/161 |
| 4,547,381 A | 10/1985 | Mason et al. ................ 426/316 |
| 4,563,184 A | 1/1986 | Korol .......................... 604/368 |
| 4,563,351 A | 1/1986 | Caslavsky et al. ........... 424/151 |
| 4,568,535 A | 2/1986 | Loesche ........................ 424/19 |
| 4,568,536 A | 2/1986 | Kronenthal et al. ........... 424/22 |
| 4,615,697 A | 10/1986 | Robinson ..................... 604/890 |
| 4,615,705 A | 10/1986 | Scales et al. .................. 623/11 |
| 4,615,937 A | 10/1986 | Bouchette ................... 428/288 |
| 4,659,609 A | 4/1987 | Lamers et al. .............. 428/194 |
| 4,661,344 A | 4/1987 | Relenyi ........................ 424/79 |
| 4,668,228 A | 5/1987 | Bolton et al. ................ 604/307 |
| 4,675,347 A | 6/1987 | Mochizuki et al. ......... 523/122 |
| 4,678,704 A | 7/1987 | Fellows ...................... 428/289 |
| 4,681,739 A | 7/1987 | Rosenblatt et al. ............ 422/37 |
| 4,689,169 A | 8/1987 | Mason et al. ........... 252/186.24 |
| 4,692,374 A | 9/1987 | Bouchette ................... 428/288 |
| 4,725,271 A | 2/1988 | Korol .......................... 604/368 |
| 4,728,498 A | 3/1988 | Theeuwes ..................... 422/29 |
| 4,735,739 A | 4/1988 | Floyd et al. ................... 252/91 |
| 4,736,467 A | 4/1988 | Schwarze et al. .............. 2/114 |
| 4,737,405 A | 4/1988 | Bouchette ................... 428/288 |
| 4,740,398 A | 4/1988 | Bouchette ..................... 428/28 |
| 4,772,492 A | 9/1988 | Bouchette ................... 427/342 |
| 4,781,974 A | 11/1988 | Bouchette et al. .......... 428/288 |
| 4,810,567 A | 3/1989 | Calcaterra et al. .......... 428/224 |
| 4,833,003 A | 5/1989 | Win et al. ................... 428/198 |
| 4,835,019 A | 5/1989 | White et al. ................. 427/387 |
| 4,837,079 A | 6/1989 | Quantrille et al. .......... 428/288 |
| 4,847,089 A | 7/1989 | Kramer et al. .............. 424/405 |
| 4,882,167 A | 11/1989 | Jang ............................ 424/468 |
| 4,883,828 A | 11/1989 | Oakes et al. ................. 523/122 |
| 4,906,464 A | 3/1990 | Yamamoto et al. ........... 424/78 |
| 4,908,209 A | 3/1990 | McIntosh, Jr. et al. ..... 424/409 |
| 4,908,381 A | 3/1990 | Greenwald et al. ......... 514/460 |
| 4,917,686 A | 4/1990 | Bayston et al. ............. 604/265 |
| 4,929,498 A | 5/1990 | Suskind et al. ............. 428/288 |
| 4,938,955 A | 7/1990 | Niira et al. .................... 424/79 |
| 4,938,958 A | 7/1990 | Niira et al. .................... 424/79 |

(Continued)

FOREIGN PATENT DOCUMENTS

DE 2625176 B2 12/1977
DE 2838523 A1 3/1980
EP 0080382 A2 6/1983

(Continued)

OTHER PUBLICATIONS

US 5,186,927, 2/1993, Withdrawn (withdrawn)
International Search Report dated Apr. 23, 2001 for International Application No. PCT/US00/34932.

(Continued)

*Primary Examiner*—Jyothsna Venkat
(74) *Attorney, Agent, or Firm*—Dority & Manning, P.A.

(57) ABSTRACT

A wiper having a controlled release anti-microbial agent therein for providing anti-microbial cleansing of surfaces is provided. The wiper is formed from an absorbent base web to which an anti-microbial formulation is adhered. The formulation includes an anti-microbial agent that is capable of being controllably released from the wiper. In some embodiments, a polymer mixture may be employed to control the rate of release of the anti-microbial agent. Various anti-microbial agents, such as metal ions and organic compounds may be employed.

38 Claims, No Drawings

U.S. PATENT DOCUMENTS

| | | | |
|---|---|---|---|
| 4,990,144 A | 2/1991 | Blott | 604/304 |
| 4,997,425 A | 3/1991 | Shioya et al. | 604/304 |
| 4,999,386 A | 3/1991 | Oakes et al. | 523/122 |
| 5,006,339 A | 4/1991 | Bargery et al. | 424/404 |
| 5,011,602 A | 4/1991 | Totani et al. | 210/484 |
| 5,019,096 A | 5/1991 | Fox, Jr. et al. | 623/1 |
| 5,023,089 A | 6/1991 | Sakamoto et al. | 424/502 |
| 5,027,438 A | 7/1991 | Schwarze et al. | 2/114 |
| 5,037,843 A | 8/1991 | Schoenberg | 514/389 |
| 5,061,485 A | 10/1991 | Oakes et al. | 424/81 |
| 5,069,907 A | 12/1991 | Mixon et al. | 424/445 |
| 5,071,648 A | 12/1991 | Rosenblatt | 424/78.06 |
| 5,087,450 A | 2/1992 | Lister | 424/402 |
| 5,108,740 A | 4/1992 | Greenwald et al. | 424/78.32 |
| 5,120,813 A | 6/1992 | Ward, Jr. | 528/28 |
| 5,126,070 A | 6/1992 | Leifheit et al. | 252/186.36 |
| 5,133,090 A | 7/1992 | Modak et al. | 2/168 |
| 5,149,469 A | 9/1992 | Komatsuzaki et al. | 264/28 |
| 5,154,920 A | 10/1992 | Flesher et al. | 514/643 |
| 5,158,778 A | 10/1992 | Donovan et al. | 424/488 |
| 5,173,535 A | 12/1992 | Abrutyn | 525/54.3 |
| 5,178,870 A | 1/1993 | Schaeken et al. | 424/405 |
| 5,187,158 A | 2/1993 | Bodor | |
| 5,211,959 A | 5/1993 | Yoshii et al. | 424/489 |
| 5,213,884 A | 5/1993 | Fellows | 428/240 |
| 5,226,434 A | 7/1993 | Britton et al. | 132/321 |
| 5,227,168 A | 7/1993 | Chvapil et al. | 421/445 |
| 5,236,703 A | 8/1993 | Usala | 424/78.36 |
| 5,238,843 A | 8/1993 | Carpenter et al. | 435/264 |
| 5,242,985 A | 9/1993 | Shih et al. | 525/326.9 |
| 5,266,329 A | 11/1993 | Riley, Jr. | 424/430 |
| 5,284,703 A | 2/1994 | Everhart et al. | 428/283 |
| 5,290,393 A | 3/1994 | Nakamura | 156/613 |
| 5,293,648 A | 3/1994 | Finley | 2/243.1 |
| 5,298,252 A | 3/1994 | Hagiwara et al. | 424/409 |
| 5,317,987 A | 6/1994 | Muller et al. | 116/206 |
| 5,320,806 A | 6/1994 | Dziabo et al. | 422/29 |
| 5,322,695 A | 6/1994 | Shah et al. | 424/448 |
| 5,324,520 A | 6/1994 | Dunn et al. | 424/435 |
| 5,330,746 A | 7/1994 | Friedman et al. | 424/49 |
| 5,336,505 A | 8/1994 | Ng et al. | 424/486 |
| 5,340,581 A | 8/1994 | Tseng et al. | 424/401 |
| 5,344,411 A | 9/1994 | Domb et al. | 604/265 |
| 5,350,624 A | 9/1994 | Georger et al. | 428/219 |
| 5,356,803 A | 10/1994 | Carpenter et al. | 435/200 |
| 5,366,732 A | 11/1994 | Zighelboim R | 424/411 |
| 5,368,852 A | 11/1994 | Umemoto et al. | 424/78.1 |
| 5,378,475 A | 1/1995 | Smith et al. | 424/473 |
| 5,389,202 A | 2/1995 | Everhart et al. | 162/103 |
| 5,407,685 A | 4/1995 | Malchesky et al. | 424/449 |
| 5,408,022 A | 4/1995 | Imazato et al. | 526/259 |
| 5,413,788 A | 5/1995 | Edwards et al. | 424/409 |
| 5,421,898 A | 6/1995 | Cavanagh | 134/7 |
| 5,429,854 A | 7/1995 | Currie et al. | 428/138 |
| 5,432,000 A | 7/1995 | Young, Sr. et al. | 428/372 |
| 5,486,381 A | 1/1996 | Cleveland et al. | 427/294 |
| 5,487,896 A | 1/1996 | Modak et al. | 424/402 |
| 5,503,840 A | 4/1996 | Jacobson et al. | 424/421 |
| 5,536,768 A | 7/1996 | Kantner et al. | 524/376 |
| 5,554,373 A | 9/1996 | Seabrook et al. | 424/400 |
| 5,556,699 A | 9/1996 | Niira et al. | 428/323 |
| 5,565,361 A | 10/1996 | Mutsakis et al. | 435/299.1 |
| 5,573,841 A | 11/1996 | Adam et al. | 428/219 |
| 5,578,124 A | 11/1996 | Cleveland et al. | 118/50 |
| 5,578,315 A | 11/1996 | Chien et al. | 424/435 |
| 5,584,877 A | 12/1996 | Miyake et al. | 623/1 |
| 5,603,921 A | 2/1997 | Bowen | 424/49 |
| 5,611,938 A | 3/1997 | Smolik et al. | 210/755 |
| 5,612,052 A | 3/1997 | Shalaby | 424/426 |
| 5,614,223 A | 3/1997 | Sipos | 424/489 |
| 5,616,315 A | 4/1997 | Masterman et al. | 424/54 |
| 5,629,081 A * | 5/1997 | Richards et al. | 424/404 |
| 5,648,003 A | 7/1997 | Liang et al. | 219/211 |
| 5,652,274 A | 7/1997 | Martin | 514/724 |
| 5,656,361 A | 8/1997 | Vogt et al. | 428/198 |
| 5,681,575 A | 10/1997 | Burrell et al. | 424/423 |
| 5,686,065 A | 11/1997 | Haney | 424/59 |
| 5,695,857 A | 12/1997 | Burrell et al. | 428/209 |
| 5,699,326 A | 12/1997 | Haas et al. | 368/327 |
| 5,702,992 A | 12/1997 | Martin et al. | 442/123 |
| 5,707,736 A | 1/1998 | Levy et al. | 428/375 |
| 5,723,132 A | 3/1998 | Tseng et al. | 424/401 |
| 5,730,994 A | 3/1998 | Askill et al. | 424/402 |
| 5,733,503 A | 3/1998 | Kowatsch et al. | 422/28 |
| 5,736,473 A | 4/1998 | Cohen et al. | 442/239 |
| 5,744,150 A | 4/1998 | Cercone | 424/404 |
| 5,747,078 A | 5/1998 | De Jong et al. | 426/9 |
| 5,753,251 A | 5/1998 | Burrell et al. | 424/426 |
| 5,763,412 A | 6/1998 | Khan et al. | 514/23 |
| 5,770,182 A | 6/1998 | Fischer | 424/49 |
| 5,770,255 A | 6/1998 | Burrell et al. | 427/2.1 |
| 5,807,563 A | 9/1998 | Askill et al. | 424/402 |
| 5,811,113 A | 9/1998 | Dorr et al. | 424/404 |
| 5,817,325 A | 10/1998 | Sawan et al. | 424/411 |
| 5,820,607 A | 10/1998 | Tcholakian et al. | 604/265 |
| 5,827,925 A | 10/1998 | Tremont et al. | 525/102 |
| 5,829,442 A | 11/1998 | Cox et al. | 128/849 |
| 5,834,051 A | 11/1998 | Woloxzko et al. | 427/2.24 |
| 5,837,274 A | 11/1998 | Shick et al. | 424/406 |
| 5,837,275 A | 11/1998 | Burrell et al. | 424/409 |
| 5,840,674 A | 11/1998 | Yatvin et al. | 514/2 |
| 5,849,311 A | 12/1998 | Sawan et al. | 424/406 |
| 5,851,551 A | 12/1998 | Tseng et al. | 424/486 |
| 5,853,760 A | 12/1998 | Cremer | 424/484 |
| 5,853,859 A | 12/1998 | Levy et al. | 428/196 |
| 5,855,208 A | 1/1999 | Askill et al. | 128/849 |
| 5,856,364 A | 1/1999 | Martin | 514/724 |
| 5,874,098 A | 2/1999 | Stevens et al. | 424/408 |
| 5,891,811 A | 4/1999 | Ashida et al. | 442/71 |

FOREIGN PATENT DOCUMENTS

| | | |
|---|---|---|
| EP | 0113254 A1 | 11/1984 |
| EP | 0351907 A2 | 1/1990 |
| EP | 0259113 B1 | 10/1990 |
| EP | 0407943 A1 | 1/1991 |
| EP | 0280571 B1 | 4/1993 |
| EP | 0285209 B1 | 5/1993 |
| EP | 0351580 B1 | 5/1993 |
| EP | 0290676 B1 | 8/1994 |
| EP | 0265906 B1 | 4/1995 |
| EP | 0677296 A2 | 10/1995 |
| EP | 0709507 A1 | 1/1996 |
| EP | 0518445 B1 | 4/1996 |
| EP | 0552151 B1 | 3/1997 |
| EP | 0761243 A1 | 3/1997 |
| EP | 0537774 B1 | 1/1998 |
| EP | 0838224 A2 | 4/1998 |
| EP | 0852148 A1 | 7/1998 |
| EP | 0869216 A1 | 7/1998 |
| EP | 0858810 A2 | 8/1998 |
| EP | 0861659 A1 | 9/1998 |
| EP | 0866103 A1 | 9/1998 |
| EP | 0875146 A1 | 11/1998 |
| EP | 0600004 B1 | 12/1998 |
| EP | 0890336 A1 | 1/1999 |
| EP | 0565301 B1 | 2/1999 |
| FR | 2431570 | 2/1980 |
| GB | 2211092 A | 6/1989 |
| WO | WO 89/05093 | 6/1989 |
| WO | WO 90/02166 | 8/1990 |
| WO | WO 91/03938 | 4/1991 |

| WO | WO 92/22221 | 12/1992 |
| WO | WO 94/26317 | 11/1994 |
| WO | WO 95/13704 | 5/1995 |
| WO | WO 96/11666 | 4/1996 |
| WO | WO 96/40361 | 12/1996 |
| WO | WO 98/24890 | 6/1998 |
| WO | WO 98/44962 | 10/1998 |
| WO | WO 041312 A2 | 5/2004 |
| WO | 064876 A2 | 8/2004 |

OTHER PUBLICATIONS

International Search Report dated Apr. 18, 2001 for International Application No. PCT/US00/34930.
Dialog Abstract 00423532/7 © 1998 of Japanese Patent JP 8205762A published Aug. 13, 1996 entitled Antimicrobial functional sheet for preserving animal protein.
Dialog Abstract 008079373/7 © 1998 of Japanese Patent JP 1257124A published Oct. 13, 1989 entitled Antibiotic aluminosilicate—obtd. by ion exchange of ions in aluminosilicate to alkaline earth or manganese ions.
Dialog Abstract 009133362 © 1999 of EP 497350A1 published Aug. 5, 1992 entitled Crystal growth on nitride semiconductor having nitride buffer layer for improved crystallinity of semiconductor growth giving improved electrical performance.
Dialog Abstract 011141997 © 1999 of CN 1080833A published Jan. 19, 1994 entitled Wet toilet paper and preparing method thereof.
Dialog Abstract 008146353 © 1999 of Japanese Patent JP 1311008A published Dec. 15, 1989 entitled Antibiotic and antifungal compsn.—comprises zeolite contg. antibiotic metal ion and resin e.g. acryl for processing.
Dialog Abstract 01824797/7 © 1998 of US 4,882,167 published Nov. 21, 1989 entitled Dry direct compression compositions for controlled release dosage forms [matrix of hydrophobic carbohydrate polymer, digestive difficulty soluble wax, fatty acid or neutral lipid.].
Dialog Abstract 004062594 © 1999 of DE 3305265A published Aug. 16, 1984 entitled Hygenic toilet seat cover for one–time use—comprises piece of crepe toilet paper cut to shape of seat and provided with self–adhesive strips for attachment to seat.
WPI Acc No.97–200913/199718 Abstract of US Patent 5118509A entitled Inducing skin tolerance to sensitising drug—by continuously and co–entensively administering drug with corticosteroid, preferably hydroconisone, to selected site.
Dialog Abstract 002274528 © 1999 of DE 2813421A published Oct. 4, 1979 entitled Perforated multiple crepe paper and tissue mat assembly—sprayed with antimycotic disinfectant and supported on abrasion–resistant backing.
Dialog Abstract 05750225/9 © 1999 entitled New Antimicrobial Agent to be Included in stainless steel products.
Dialog Abstract 00365165/7 © 1998 of Japanese Patent JP 7123963A published May 16, 1995 entitled Antimicrobial water absorbing sheet.
Dialog Abstract 00162494/7 © 1998 of West German Patent EP 206285 published Jun. 27, 1985 entitled Filter cartridge for upgrading drinking water quality.
Dialog Abstract 008153158/7 © 1998 of Japanese Patent JP 1316303A published Dec. 21, 1989 entitled Hydrous antimicrobial agent—comprises inorganic carrier contg. antimicrobial agent and nonwoven fabric of e.g. polyester resin layer.
Abstract 009382194 of US Patent 51 86927A published Feb. 16, 1993 entitled Antimicrobial compsn. for oral hygiene—comprises particles having an outer surface onto which antimicrobial agent has been adsorbed.
Derwent Abstract 010600920 © 1999 of Patent AU 9514811A published Jan. 25, 1996 entitled Antimicrobial laminate for bags for foodstuffs for gradual release—comprises substrate impervious to steam and pervious firm superposed through adhesive layer contg. polyallyl isothiocyanate cyclodextrin cpd.
Abstract 009382274 of US Patent 5187158A published Feb. 16, 1993 entitled New O–dihydropyridylcarbonyl prodrug derivs. of ribovarin–used for site specific and sustained delivery of antiviral a ent to the brain, and is retained in the brain after oxidn. to quat. pyridinium form.
Abstract 009230315 of CA Patent 1307738C published Sep. 22, 1992 entitled Liposome(s) having out bilayer with asymmetric distribution—comprise ionisable lipid or ionisable protein, useful as a drug delivery systems.
Abstract 008636625 of CA Patent 2020966A published Jan. 13, 1991 entitled Biocompatible film–forming topical delivery system—comprises active salt of carboxylic acid–functional polymer with therapeutic agent.
Dialog Abstract 010620478 © 1999 of CA 2134498A published Nov. 26, 1995 entitled Cove base for building wall—has elongate flat plate containing antimicrobial agent released over time.
Abstract 003667575 of DE 3134152A published Mar. 17, 1983 entitled Antimicrobial carrier esp. for delivery to bone—is metal or plastics coil opt. with polymer coating.
Abstract 004653629 of EP 184629 A published Jun. 18, 1986 entitled Microbicidal tub for urine drainage bag—passively releases antimicrobial on emptying to prevent infection.
Dialog Abstract 009588282 © 1999 of EP 558913 Al published Sep. 9, 1993 entitled Two component minocycline controlled release delivery system—comprises initial loading of rapid release granules and sec. loading of blended polymer coated spherical granules.
Dialog Abstract 011058050 © 1999 of EP 748634 A2 published Dec. 18, 1996 entitled Surgical implant, esp. for use as vascular prosthesis—produced from or comprising resorbable material contg. antimicrobial agent, esp. gentamycin crobefate.
Abstract 004440566 © 1999 of JP 60181029 A published Sep. 14, 1985 entitled Sustained release drug. prepn.—involves mixing a e.g. peptide, protein, antimicrobial or antitumor drug with lactic acide (co) polymer.
Abstract 008370474 © 1999 of JP 2180694 A published Jul. 13, 1990 entitled Contimination preventing system for sterile water producing system—includes container contg. gradual release alkali cpd. and having discharge opening dia. preventing contamination.
Abstract 009176092 © 1999 of JP 4208205A published Jul. 29, 1992 entitled Sustained release antimicrobial ally isothiocyanate compsn.—prepd. by dissolving allyl isothiocyanate in glycerine ester or high alcohol ester.
Abstract 010615628 © 1999 of JP 8012511A published Jan. 16, 1996 entitled Prodn. of sustained–release antimicrobial agent used to maintain freshness of e.g. processed food—comprises dissolving volatile antimicrobial component in organic solvent, adding starch and removing solvent.

Abstract 010853168 of JP 8165210 A published Jun. 25, 1996 entitled Prodn. of antimicrobial agents—involves radically polymensing poly(meth)acryllic acid ester cpds. in organic solvent contg. aq. soln. of silver, copper or zinc ions.

Abstract of 010853169 of JP 8165211A published Jun. 25, 1996 entitled Prodn. of antimicrobial agents—copolymerising polyacryllic or polymethacryclic acid ester cpds. and silver, copper or zinc (meth) acrylic acid salts, inorganic solvent.

Dialog Abstract 011029508 of JP 8277204A published Oct. 22, 1996 entitled Sustained release microorganism control prepn—prepd by coating liq drop contg microorganism control agent with hydrophobic until microparticle silicon oxide power.

Abstract 011665622 of JP 9315927A published Dec. 9, 1997 entitled Antimicrobial cosmetic—comprises water containing components released from copper or copper alloy at effective doses which give antimicrobial activity.

Abstract 011393337 of Rusian Patent RU 2071323C1 published Jan. 10, 1997 entitled Antiviral sustained release preparation for treating acute respiratory diseases and herpes—contg. salt based on adamantyl–methylamine cpd. and copolymer derived from vinyl alcohol and N–vinylamido–succinic acid.

Abstract 007135943 of WO 8702576A published May 7, 1987 entitled Vaginal delivery systems —. consist of viscous emulsion with (non) Iipoidal phases, which adheres to vaginal wall.

Abstract 007673497 of WO 8807853A published Oct. 20, 1988 entitled Liposomal vesicles for sustained intraperitoneal delivery—comprise therapeutic agent encapsulated in phosphatidyl choline–contg. lipid vesicle.

Abstract 009122425 of WO 9211042 A1 published Jul. 9, 1992 entitled Compsns, for disinfecting contact lenses–comprising aq. hydrogen peroxide, and a hydrogen peroxide–r-educing agent to enhance antimicrobial activity, from peroxidase.

Abstract 009342695 of WO 93100115 A1 published Jan. 7, 1993 entitled Adhesive patch for controlled release of vapours to surroundings—useful for therapeutic agents, insecticides, insect repellants, perfumes, etc.

Abstract 009382714 of WO 9302717 A1 published Feb. 18, 1983 entitled Adhesive prod. used as surgical or medical dressing—comprises emulsion adhesive contg. medicament, coated on support, giving good antimicrobial activity.

Dialog Abstract 009440678 of WO 9306921 A1 published Apr. 15, 1993 entitled Particles with internal lyotropic liq. crystalline and lamellar surface phases–form stable dispersions useful for e.g. sustained drug delivery, antigen presentation, nucleic acid transport etc.

Dialog Abstract 010298861 of WO 9513704 A1 published May 26, 1995 entitled Material for sustained release of antimicrobial metal, esp. silver—has atomic disorder so that ions etc., are released into electrolytes at increased rate, useful e.g. for coatin medical devices.

Dialog Abstract 010426917of WO 9524430 A2 published Sep. 14, 1995 entitled New block and graft copolymers—comprising pH–sensitive and temp. sensitive polymer components, useful for drug delivery for sustained and controlled release.

Abstract Document No. 5595750 published Jan. 21, 1997 entitled Antimicrobial particles of silver and barium sulfate or zinc oxide.

Abstract Document No. 5869073 published Feb. 9, 1999 entitled Antimicrobial liquid compositions and methods for using them.

Dialog Abstract 010936562 © 1999 of WO 9628141 A1 published Sep. 19, 1996 entitled Muco–adhesive granules contg carbomer and inert filler—for sustained release of pharmaceutical in gastro–intestinal tract.

Dialog Abstract 011905997 © 1999 of WO 9824007A published Jun. 4, 1998 entitled Single line automated fluid delivering method for dental unit water line treatment—involves locking out operating control of consumable water or aqueous solution delivery device to prevent operation of device during antimicrobial flushing.

Dialog Abstract 008128186 © 1999 of ZA 8809601A published Oct. 25, 1989 entitled Implants contg. antimicrobial agent for slow release in animals.

Dialog Abstract 02495825/9 © 1999 entitled AK Steel signs pact for healthier coating.

Publication by Wipex entitled Disinfectant Wipes with Indicator Stripes.

Article published in Letters in Applied Microbiology 1993, vol. 16 pp. 173–177 entitled An in–use study of the relationship between bacterial contamination of food preparation surfaces and cleaning cloths.

Article published in Journal of Applied Bacteriology 1990, vol 68, p. 271–278 entitled The survival and transfer of microbial contamination via cloths, hands and utensils.

Article published in J Antibact. Antifungi Agents, vol. 22, No. 9, p. 531–536, 1994. entitled Antimicrobial Activities of Silver and Copper Ions.

Article published by BF Goodrich in http://www.bfsolutions.com entitled Hycar Reactive Liquid Polymers—The Key To Building Superior Products.

Article published by Sybron Chemicals, Inc. of Birmingham, NJ entitled XAMA–7 and lonac Poly functional Aziridine.

Article adapted from Standard Methods for the Examination of Water and Wasterwater (method 8167).

Article published in Springer–Verlag Berlin Heidelberg New York 1980 by Erich Lueck entitled Antimicrobial Food Additives—Characteristics—Uses—Effects.

Abstract of Article published in Hy–LiTE Data Logger Operators Manual by EM Science.

* cited by examiner

WIPER CONTAINING A CONTROLLED-RELEASE ANTI-MICROBIAL AGENT

The present invention is based on provisional patent application Ser. No. 60/173,400 filed Dec. 28, 1999, and priority is hereby claimed therefrom.

FIELD OF THE INVENTION

The present invention generally relates to a wiper, such as the type used to disinfect hard surfaces in food service and medical applications. More particularly, the present invention is directed to a wiper having an anti-microbial agent such that it can be controllably released over an extended period of time.

BACKGROUND OF THE INVENTION

Microbial contamination can have a detrimental effect on any item ordinarily used by consumers or merchants, particularly items used in the medical and food service industries. For example, due to various bacterial outbreaks, there have been at least 200 food poisoning deaths reported in the last 10 years. Moreover, more Americans die from hospital infections each year than from car accidents and homicides combined.

Much of this contamination occurs due to the migration of microorganisms from hard surfaces such as table tops and counter tops to food and to food handlers, thence to food. For example, in the food service industry, contamination commonly occurs on stainless steel surfaces used for food preparation. Various food products are prepared on hard surfaces such as counters, tables, and the like. Bacteria from these products will often collect on such surfaces and, if the surface is not cleansed regularly, can transfer from product to product or from product to the preparer. Numerous studies indicate that cross-contamination occurs as a result of a microorganism coming in contact with a person's hands or with a cleaning cloth and thereafter contaminating other items touched by the cloth or hands, such as equipment or other surfaces.

As a result, wipers that contain anti-microbial agents have been employed to prevent such surface and cloth contamination. Currently, most of these anti-microbial wipers are impregnated with anti-microbial agents that are delivered to the user in a pre-moistened form. However, the disinfecting agent within the wiper can be readily exhausted after only a few washings and rinsings to remove dirt after a period of use. Thus, it is believed that such pre-moistened wipers either inhibit growth on the wipers and/or the hard surfaces cleaned only mildly or may only be used for a limited number of wipes.

Some anti-microbial wipers have been developed that are not pre-moistened. For example, one such anti-microbial wiper that can be delivered in a dry condition is disclosed in U.S. Pat. No. 5,213,884 to Fellows. In the Fellows patent, a wiper is disclosed that contains a hot melt adhesive powder mixed with a chlorine release agent. The adhesive powder and chlorine release agents are incorporated into a tissue suitable for use in the disinfection of hard surfaces.

Although the wiper disclosed by Fellows can be delivered in a dry form, it apparently fails to provide sufficient disinfection over an extended period of time—similar to pre-moistened wipers. After being contacted with water, the release of the anti-microbial agent in such wipers capable of being delivered in a dry state occurs readily without control. This prevents the wiper from sustaining its anti-microbial activity after repeated washings and rinsings.

Another anti-microbial wiper has been marketed by Pal International, Inc. of England under the name WIPEX®. According to the sales literature, this wiper contains poly (hexamethylenebiguanide hydrochloride), alkyldimethybenzyl ammonium chloride, and the disodium salt of ethylenediaminetetraacetic acid (E.D.T.A.). In addition, the wipers include indicator stripes that are stated to fade gradually as the disinfectants are depleted from the wiper. It is believed that U.S. Pat. No. 4,311,479 to Fenn et al. is related to this particular anti-microbial cloth. It is believed, however, that these wipers have not proven to be very effective in reducing certain bacterial activity. Also, it is believed that they might retain only limited anti-microbial activity after several rinses.

In U.S. Pat. No. 4,906,464, Yamamoto et al. describe the preparation of a dispersion of an antibiotic powder, such as a zeolite or an amorphous aluminosilicate whose ion exchange ions have been partially or completely ion-exchanged with antibiotic metal ions and/or ammonium, in a dispersion medium, such as a thermoplastic resin, a polyol, an alcohol, a higher alcohol, a higher fatty acid, or a resin emulsion. The components are mixed at a reduced pressure and at a temperature at which the dispersion medium is a liquid, and where the viscosity of the dispersion is between 2,000 cp. to 200,000 cp. Such dispersions were applied to the surface of nylon, rayon and cotton cloths, and it was shown that the treated cloths apparently had the capacity to kill bacteria within 24 hours in solutions that were sprayed onto the treated cloths. A principal object of the invention was to provide a method for uniformly dispersing antibiotic powder in a dispersing medium such as a resin.

In U.S. Pat. No. 4,938,958, to Niira et aL, an antibiotic resin composition was described as including a resin and an antibiotic zeolite in an amount of from 0.05% to 80% by weight of the composition, where the zeolite contained from 0.1% to 15% by weight of silver and from 0.5% to 15% by weight of ammonium ions. In U.S. Pat. No. 4,938,955, a group from the same assignee disclosed an antibiotic resin composition that included a resin, an antibiotic zeolite like the one just described, and a discoloration inhibitor. An object of the invention was to provide an antibiotic resin composition which does not discolor with time and which exhibits excellent antibiotic effect.

The same type of antibiotic zeolite was incorporated into a transparent self-supporting antibiotic film (U.S. Pat. No. 5,556,699). The film was of an organic polymer and was not over 10 microns in thickness, and included 25 to 100 mg of the antibiotic zeolite per square meter. It was stated that the antibiotic activity was fully effective and complete (100%). An object of the invention was to provide an antibiotic zeolite-containing film having a relatively low content of antibiotic zeolite, which exhibits a satisfactory antibiotic action and is also transparent. Applications were included that showed the lamination of the film to a substrate, such as a resin film, and it was suggested that the laminated film could further be laminated to a layer of resin, metal, or paper to form sheets or other molded products. The molding of such a laminated film to a toothbrush was demonstrated.

In U.S. Pat. No. 4,615,937, to Bouchette, an antimicrobially active wet wiper is described that comprises bonded fibers of a nonwoven web, which are bonded together by a uniformly distributed binder. An antimicrobial agent is bound to the fibers and the binder in a manner that prevents the agent from substantively diffusing from the fibers or the binder, whether the wiper is wet or dry. A purpose of the invention is to prevent the transfer of the anti-microbial agent to a user's skin, where it might leave an irritating residue. Apparently, therefore, any liquid that would be left by the wiper on a wiped surface would be substantially free of the anti-microbial agent.

Thus, it remains that a need currently exists for a more effective wiper that disinfects hard surfaces and inhibits cross-contamination. In particular, a need exists for a wiper that contains an anti-microbial agent that is slowly released when contacted by water, thereby allowing the wiper to provide an anti-microbial solution and to sustain its anti-microbial effectiveness after repeated washing and rinsing operations.

SUMMARY OF THE INVENTION

Accordingly, an object of the present invention is to provide a wiper suitable for use in disinfecting hard surfaces.

It is another object of the present invention to provide a wiper containing an anti-microbial agent that can remain effective after repeated washing and rinsing.

Still another object of the present invention to provide a wiper containing an anti-microbial agent that can remain effective after repeated washing and rinsing by releasing the anti-microbial agent at a controlled rate.

It is another object of the present invention to provide a wiper in which the cloth-like base web is applied with a formulation containing an anti-microbial agent.

Another object of the present invention is to provide a formulation that contains an anti-microbial agent and a polymer.

It is another object of the present invention to provide a formulation that contains an anti-microbial agent and a polymer that can retain its strength and adhesion properties after being applied to the base web, and thereafter creped and cured.

These and other objects of the present invention are achieved by providing a wiper capable of providing liquid anti-microbial solution after numerous rinse cycles. The wiper generally includes a controlled release anti-microbial formulation comprising an anti-microbial agent, which formulation is adhered to an absorbent, cloth-like web which retains liquid after each rinse cycle. The combination of the anti-microbial formulation and the retained liquid in the wiper is adapted so that the formulation releases sufficient anti-microbial agent into the retained liquid after each of at least five normal rinse cycles so that the retained liquid is an anti-microbial solution. In certain embodiments, the anti-microbial formulation can include an anti-microbial agent encapsulated in, adsorbed to, or as a part of a particle or microcapsule. In certain embodiments, the anti-microbial formulation may be in the form of an anti-microbial agent that is coated by or enclosed in a polymer coating.

In accordance with the present invention, any material commonly used in the art to manufacture cloths, such as wipers, can be used as the base web. In particular, a base web of the present invention is typically made from a nonwoven polymeric or paper-based web. More particularly, a base web of the present invention can be made from pulp fibers, synthetic fibers, thermomechanical pulp, or mixtures thereof such that the web has cloth-like properties. For instance, the base web can be made from softwood pulp fibers, such as Northern softwood Kraft fibers, redwood fibers and pine fibers. Moreover, the base web can also include staple fibers, such as polyolefin fibers, polyester fibers, nylon fibers, polyvinyl acetate fibers, cotton fibers, rayon fibers, non-woody plant fibers, and mixtures thereof.

A wiper of the present invention also includes an anti-microbial formulation that can be adhered to the base web.

In accordance with the present invention, the formulation can contain an anti-microbial agent that is adapted to being released from the anti-microbial formulation at a controlled rate. In general, an anti-microbial agent of the present invention can be made from any additive that can be used as a disinfectant in wipers.

As stated, an anti-microbial formulation of the present invention may also comprise a polymer or polymer mixture that can aid in binding the anti-microbial agent to the fibers and controlling the release of the anti-microbial agent from the wiper. Although not required, the polymer(s) in the polymer mixture can, in some embodiments, be capable of swelling in water. In general, any such water-swellable polymer is suitable for use in the present invention. Examples of water swellable polymers that can be used in the present invention include adhesives such as acrylates, styrene butadiene, vinyl chlorides, methacrylates, acrylics (such as carboxylated acrylics), and vinyl acetates (such as self cross-linking ethyl vinyl acetate, hydrolyzed polyvinyl acetate, or non-cross-linking ethyl vinyl acetate). In some particular embodiments, the water-swellable polymer can comprise carboxylated acrylics.

In certain embodiments of the present invention, a polymer mixture may also comprise a polymer that can become cross-linked when dried. The use of cross-linkable polymers, such as latex adhesives, can allow the release of the anti-microbial agent to be further controlled. Specifically, increasing the amount of cross-linking in the adhesive can result in less swelling, which in turn results in a faster release of the anti-microbial agent when the wiper is contacted with water.

In accordance with the present invention, other various components can also be added to the polymer mixture of the anti-microbial formulation as desired. For example, plasticizers, such as glucose triacetate, can be added to the polymer mixture to aid in the migration of the anti-microbial agent to the polymer surface. In addition to plasticizers, cross-linking agents, catalysts, thickeners, defoamers, colorants, water, etc., can also be added to an anti-microbial formulation of the present invention. Furthermore, chemicals such as stabilizers, viscosity modifiers, composite particles, or surfactants, can be added as well.

In some embodiments, a visual sensor, colorant, or dye can be incorporated into the subject wiper to indicate when the anti-microbial agent has been exhausted. For example, sodium thiosulfate and various blue dye mechanisms, such as those employed in the WIPEX® wipes may also be employed. Furthermore, a visual sensor mechanism disclosed in co-pending and co-owned U.S. Provisional Application entitled "Use-Dependent Indicator System for Absorbent Articles", which is incorporated herein by reference thereto, can also be utilized in conjunction with a wiper of the present invention.

According to the present invention, the release rate of the anti-microbial agent from the anti-microbial formulation can generally be controlled in a variety of ways. In one embodiment, for example, the release rate of the anti-microbial agent can be controlled by the incorporation of the anti-microbial agent as a part of a system that provides controlled release properties. For instance, certain anti-microbial agents, such as silver can be included as an ion that is bound by an ion exchange resin, such as a zeolite. Such systems can be supplied in the form of powders and are adapted to release the anti-microbial agent—silver ions, in this case, from a wiper at a controlled rate. Moreover, other mechanisms that can aid in controlling the release rate of the anti-microbial agent include varying the size of solid anti-microbial agent particles, the use of polymerization chemistries, the employment of at least partially encapsulated solid anti-microbial particles, the use of porous absorbents, the use of soluble binders, or combinations thereof.

An alternative to providing the anti-microbial agent as part of a system that has controlled release properties, is the provision of a formulation in which the release of the anti-microbial agent from the wiper can also be controlled by an anti-microbial agent that is contained within, or in a mixture with a polymer or polymer mixture. In particular, the components of the polymer mixture can be selected and varied to control the release of the anti-microbial agent without adversely affecting the strength and adhesion properties of the polymer mixture. For example, the release rate of the anti-microbial agent can be controlled by varying the type and amount of polymer, cross-linking agent, plasticizer, etc., used in a polymer mixture of the present invention.

Furthermore, in some embodiments, the method of applying a formulation of the present invention to the base web can also aid in controlling the release of the anti-microbial agent. Generally, a formulation of the present invention can be applied to the base web by any method of application, including, but not limited to, print, print crepe, spray, blade, saturant, coating, droplet throw, and foam application methods. For example, in one embodiment, the formulation can be applied to at least one side of the base web. In certain embodiments, the formulation may be applied to both sides of the base web.

In one embodiment, the formulation can be applied onto the base web in a pre-selected pattern using a print roll. The pre-selected pattern used to apply the formulation can be, in one embodiment, a reticular interconnected design. Alternatively, the pre-selected pattern can comprise a succession of discrete shapes, such as dots. In a further alternative embodiment of the present invention, the pre-selected pattern can be a combination of a reticular interconnected design and a succession of discrete shapes.

The formulation can also, in some embodiments, be applied to the base web such that it covers less than 100%, and more particularly from about 10% to about 60% of the surface area of each side of the web. Moreover, in some embodiments, the formulation can be applied to each side of the base web in an amount of up to about 2% to about 8% by weight of the web. Once applied, the formulation can penetrate the base web in an amount from about 10% to about 60% of the total thickness of the web.

In some embodiments, after applying the formulation to the base web, the web can then be creped to increase the softness, absorbency, and bulk of the web. Depending on the application, one or both sides of the web can be creped. Furthermore, the base web can be dried and cured after applying the formulation and creping, if necessary. Curing can increase the strength of the base web, as well as aid in controlling the release time of the anti-microbial agent. In one embodiment, for example, controlling the degree of polymer curing can enhance the control over the amount of swelling by a polymer when the wiper is contacted with water. This, in turn, may provide control over the release rate of the anti-microbial agent.

Other objects, features and aspects of the present invention are discussed in greater detail below.

DETAILED DESCRIPTION OF REPRESENTATIVE EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

In general, the present invention is directed to a wiper containing an anti-microbial agent that is incorporated into an anti-microbial formulation that is applied to a base web such that the anti-microbial agent can be released from the anti-microbial formulation at a controlled rate until the anti-microbial agent is exhausted. When the subject wiper is contacted with water, a certain amount of water is absorbed by the absorbent web and, when the wiper is wrung out, or permitted to drip until excess water has been lost, the absorbent web retains a certain amount of liquid. It has been discovered that by incorporating an anti-microbial agent within a formulation that is adhered to the web, the anti-microbial agent can be released at a controlled rate to bring the content of the anti-microbial agent in the retained liquid to a level where the retained liquid can act as an anti-microbial solution. Sufficient anti-microbial agent can be incorporated into the anti-microbial formulation and a sufficient amount of the formulation can be adhered to the web, so that only a part of the anti-microbial agent is released from the formulation during each normal rinse cycle and the wiper can continue to provide the retained liquid as an anti-microbial solution after multiple rinsing cycles.

An advantage of the subject wiper is that stronger anti-microbial agents can be employed than if such agents were used directly and not as a part of the subject anti-microbial formulation, and multiple washing and rinsing cycles can be realized without completely and quickly depleting the anti-microbial qualities of the wiper.

As used herein, the terms "anti-microbial agent" refers to a material that is capable of killing or reducing the growth rate of common disease causing bacteria.

The terms "anti-microbial solution", as used herein, refer to a liquid having in solution an amount of an anti-microbial agent that is sufficient to kill or reduce the growth rate of strains of common disease causing bacteria as compared with the same liquid without that amount of anti-microbial agent. In some embodiments of this invention, it is possible for the anti-microbial solution to act as a sanitizer solution or a disinfectant solution.

As used herein, the terms "anti-microbial formulation" refer to a combination of an anti-microbial agent and a material that serves to modulate the release rate of the agent when it is in contact with a liquid. The formulation, in some instances, can also adhere the agent to the web. When it is said that a material "modulates the release rate of the agent", or provides a "controlled release" feature, it is meant that the material reduces the rate of release of the agent into a liquid from what the rate would be if no such material were present.

As used herein, the terms "rinse cycle" and "washing and rinsing", mean the same thing and refer to the steps of contacting a wiper with water, followed by free drip and then by wringing or squeezing. A "normal rinse cycle", as those terms are used herein, refers to a manual rinse of the wiper with water, followed by hand wringing, as would typically occur under normal use conditions.

The terms "residual liquid", as used herein, refer to the liquid that is retained in a wiper after a rinse cycle.

In accordance with the present invention, an anti-microbial surface wiper is provided that contains a base web to which is adhered an anti-microbial formulation. In particular, an anti-microbial formulation of the present invention contains an anti-microbial agent that can be released at a controlled rate.

The process of forming a wiper made according to the present invention involves first forming a base web material. A base web of the present invention can generally be made from any absorbent material used in the art for wipers. In particular, any nonwoven polymeric or paper-based, generally absorbent, web is suitable for use in the present invention. Examples include webs made from pulp fibers, synthetic fibers, and mixtures thereof such that the web has cloth-like properties. In addition, the web can be a co-form material such as disclosed in U.S. Pat. No. 4,100,324 to Anderson et al. and U.S. Pat. No. 5,350,624 to Georger et al., which are incorporated herein in their entireties by reference thereto. The wipers may be packaged and made according to the disclosures of U.S. Pat. Nos. 4,833,003 and 4,853,281 to Win et al.

For example, the material used to make a cloth-like base web of the present invention can include pulp fibers either alone or in combination with other types of fibers. The pulp fibers used in forming the base web may be softwood fibers having an average fiber length of greater than 1 mm and particularly from about 2 to 5 mm based on a length-weighted average. Such fibers can include Northern softwood Kraft fibers, redwood fibers and pine fibers. Secondary fibers obtained from recycled materials may also be used.

In one embodiment, synthetic fibers, such as staple fibers (and filaments) can be also added to increase the strength, bulk, softness and smoothness of the base web. Staple fibers can include, for instance, polyolefin fibers, polyester fibers, nylon fibers, polyvinyl acetate fibers, cotton fibers, rayon fibers, non-woody plant fibers, and mixtures thereof. In general, staple fibers are typically longer than pulp fibers. For instance, staple fibers typically have fiber lengths of 5 mm and greater.

The staple fibers added to the base web can also include bicomponent fibers. Bicomponent fibers are fibers that can contain two materials such as, but not limited to, two materials in a side-by-side arrangement or in a core and sheath arrangement. In a core and sheath fiber, the sheath polymer will usually have a lower melting temperature than the core polymer. For instance, the core polymer, in one embodiment, can be nylon or a polyester, while the sheath polymer can be a polyolefin such as polyethylene or polypropylene. Such commercially available bicomponent fibers include CELBOND® fibers marketed by the Hoechst Celanese Company.

The staple fibers used in a base web of the present invention could also be curled or crimped. The fibers can be curled or crimped, for instance, by adding a chemical agent to the fibers or subjecting the fibers to a mechanical process. Curled or crimped fibers may create more entanglement and void volume within the web and further increase the amount of fibers oriented in the –Z direction as well as increase web strength properties.

In general, base webs made according to the present invention can be made exclusively from synthetic fibers, such as fibers made from various polymeric materials. The synthetic fibers can be staple fibers or other various types of fibers or filaments. As described above, a base web of the present invention can also be made from a mixture of synthetic fibers and pulp fibers.

In one embodiment, when forming an anti-microbial wiper containing pulp fibers, the staple fibers can be added to the base web in an amount from about 5% to about 30% by weight and particularly from about 10% to about 20% by weight. For example, short staple fibers made from a polyester or polyolefin can be added to the base web. The fibers can have a length of from about % of an inch to about 1 inch. The fibers can be mixed homogeneously with the pulp fibers in forming the web. Staple fibers can increase the strength and softness of the final product.

Besides pulp fibers and spunbonded fibers, thermomechanical pulp fibers can also be added to the base web. Thermomechanical pulp, as is known to one skilled in the art, refers to pulp that is not cooked during the pulping process to the same extent as conventional pulps. Thermomechanical pulp tends to contain stiff fibers and has higher levels of lignin. Thermomechanical pulp can be added to the base web of the present invention in order to create an open pore structure, thus increasing bulk and absorbency and improving resistance to wet collapse.

When present, the thermomechanical pulp can be added to the base web in an amount of from about 10% to about 30% by weight. When using thermomechanical pulp, a wetting agent may also be added during formation of the web. The wetting agent can be added in an amount less than about 1% and, in one embodiment, can be a sulphonated glycol.

The fiber furnish used to form the base web can also be treated with a chemical debonding agent to reduce inner fiber-to-fiber strength. Suitable debonding agents that may be used in the present invention when the base web contains pulp fibers include cationic debonding agents such as fatty dialkyl quaternary amine salts, mono fatty alkyl tertiary amine salts, primary amine salts, imidazoline quaternary salts, and unsaturated fatty alkyl amine salts. Other suitable debonding agents are disclosed in U.S. Pat. No. 5,529,665 to Kaun, which is incorporated herein in its entirety by reference thereto.

In certain embodiments, the debonding agent can be an organic quaternary ammonium chloride. In these embodiments, the debonding agent can be added to the fiber slurry in an amount of from about 0.1% to about 1% by weight, based on the total weight of fibers present within the slurry.

In one embodiment, a base web of the present invention as described above can be hydraulically entangled (or hydroentangled) to provide further strength. Hydroentangled webs, which are also known as spunlace webs, refer to webs that have been subjected to columnar jets of a fluid that cause the fibers in the web to entangle. Hydroentangling a web typically increases the strength of the web. Thus, according to the present invention, in order to increase the strength of a web, a base web of the present invention can be hydroentangled. For example, in a certain embodiment, the base web can comprise HYDROKNIT®, a nonwoven composite fabric that contains 70% by weight pulp fibers that are hydraulically entangled into a synthetic continuous spunbonded filament material. HYDROKNIT® material is commercially available from Kimberly-Clark Corporation of Neenah, Wis. HYDROKNIT® is further disclosed in U.S. Pat. No. 5,284,703 to Everhart et al. which is incorporated herein in its entirety by reference thereto.

In addition, the base web of the present invention can be a spunbonded, meltspun or meltblown web, or can be any other type of woven or nonwoven fabric that is absorbent to liquid water and is capable of having the anti-microbial formulation adhered thereto. In addition, the web can be a co-form material such as disclosed in U.S. Pat. No. 4,100,324 to Anderson et al. and U.S. Pat. No. 5,350,624 to Georger et al., which are incorporated herein in their entireties by reference thereto.

In accordance with the present invention, the process of forming an anti-microbial wiper also typically involves forming an anti-microbial formulation that can be applied to the base web. A component of the anti-microbial formulation is an anti-microbial agent. The anti-microbial agent can generally include any anti-microbial compound or material that can be used as a disinfectant in wipers. Useful anti-microbial agents include silver ions, free chlorine generating material, such as hypochlorites—in particular sodium and calcium hypochlorite—, and can also include compounds that generate chlorine dioxide, such a chlorates, as well as quaternary amines—such as alkyl aryl benzonium chloride—, halogens other than chlorine, materials such as Triclosan, and other metal ions with anti-microbial activity.

In one embodiment, where the anti-microbial agent is chlorine dioxide, the anti-microbial formulation can be a chlorine dioxide generating material containing sodium chlorate and an acid moiety. The chlorate and the acid compounds can be separated from each other in the formulation, such as by supplying each of them in a coated form, where the coating releases the contents when contacted with water, or alternatively, the two compounds could be placed in different parts of the web so that they would not come into contact with each other until the web was wetted with water. However, when a wiper containing such a formulation is contacted with water, the chlorate and the acid come into contact and chlorine dioxide is formed.

Some examples of systems that can be used to generate chlorine dioxide, for instance, are disclosed in U.S. Pat. Nos. 4,681,739; 4,689,169; 5,227,168; 5,126,070; and 5,407,685, all of which are incorporated herein in their entireties by reference thereto. Another anti-microbial agent that could be employed is disclosed in U.S. Pat. No. 5,837,274 to Shick et al., which is also incorporated herein in its entirety by reference thereto.

As discussed above, the anti-microbial formulation of the present invention can be a particle or coating that contains an anti-microbial agent and also provides, without modification, a certain amount of controlled release characteristics for the agent. These formulations can be adhered to the base web without further modification, or they can be used with an additional polymer as part of a coating that is adhered to the base web.

In certain embodiments, a silver-zeolite complex can be utilized as the anti-microbial formulation to provide controlled release of the anti-microbial agent—silver ions. One commercially available example of such a controlled-release silver formulation has been sold as a fabric by AgION® Technologies L.L.C. (formerly K.B. Technologies, Inc.) under the name GUARDTEX®, and is constructed from polyester and rayon and contains a silver-zeolite complex. Other suitable silver-containing anti-microbial agents are disclosed in Japanese Unexamined Patent No. JP 10/259325, which is incorporated herein by reference. Moreover, in addition to silver-zeolites, other metal-containing inorganic additives can also be used in the present invention. Examples of such additives include, but are not limited to, copper, zinc, mercury, antimony, lead, bismuth, cadmium, chromium, thallium, or other various additives, such as disclosed in Japanese Patent No. JP 1257124 A and U.S. Pat. No. 5,011,602 to Totani et al., which are incorporated herein by reference. In some embodiments, the activity of the anti-microbial agent can be increased, such as described in U.S. Pat. No. 5,900,383 to Davis et al., which is also incorporated herein by reference.

The anti-microbial formulation can also be formed by combining an anti-microbial agent with a polymer or a mixture of polymers. Such a formulation can provide controlled release characteristics for the anti-microbial agent by controlling the properties of the polymer, and how the polymer/anti-microbial agent formulation is applied to the base web. For example, such a formulation may be simply particles of an anti-microbial agent that are mixed into a polymer prior to applying the polymer/agent mixture to the web. The polymer can then be cured or cooled to form a solid. The reduced rate of mass transfer of the agent through the solidified polymer provides the method of controlling the rate of release of the agent. Almost any form of an anti-microbial agent can be used with a polymer, including powders, microspheres, controlled-release formulations as described above, gels, liquids, or the like.

The release rate of anti-microbial agents that are a part of a polymer matrix can also be controlled by varying particle size, using polymerization chemistries, encapsulation, using porous absorbents, using soluble binders, and other similar technologies can be employed to enhance the ability to control the amount of anti-microbial agent released over a given period of time.

When an anti-microbial formulation of the present invention is formed by partially or completely coating or encapsulating an anti-microbial agent to provide further control over the release rate, any coating known in the art to reduce the release rate of the agent can be used. For example, in one embodiment, an aqueous emulsion of an acrylic polymer may be used to coat a particulate calcium hypochlorite anti-microbial agent. In another embodiment, a microcrystalline wax coating may be employed. In yet another embodiment, polyethylene can be used. Moreover, to sufficiently reduce solubility when using a coating, it is not generally necessary to completely coat the particles. For instance, in various embodiments, a 20% acrylic polymer coating, a 33.5% acrylic polymer coating, or a 60% microcrystalline polyethylene wax coating may be used. The percentages refer to the weight of the polymer as a percentage of the weight of the anti-microbial agent. The partially coated particles would, in this case, form the anti-microbial formulation.

Various other components can be added to a formulation of the present invention to enhance control over the release rate of the anti-microbial agent. In one embodiment, for example, a polymer mixture can be added to the formulation.

A polymer mixture of the present invention can generally provide a variety of benefits. For example, the polymer mixture can enhance the strength and adhesion characteristics of the base web. Moreover, the polymer mixture can also aid in binding the anti-microbial agent to the base web, as well as enhancing the control over the release time of the anti-microbial agent. In some embodiments, the components of the polymer mixture are such that the entire mixture is capable of swelling or "blooming" when contacted with water. In some cases, such "blooming" of the polymer mixture is believed to modulate the release rate of the anti-microbial agent. As such, a polymer mixture of the present invention can generally comprise any of a variety of materials, at differing amounts, as long as the overall mixture is capable of binding the anti-microbial agent to the base web and also modulating the release rate of the anti-microbial agent therefrom.

In this regard, one embodiment of the present invention includes a polymer mixture containing a polymer. For example, various adhesives can be used as polymers in the present invention. Examples of adhesives that can be used include, but are not limited to, acrylates, styrene butadiene, vinyl chlorides, methacrylates, acrylics (such as carboxylated acrylics), and vinyl acetates (such as self cross-linking ethyl vinyl acetate, hydrolyzed polyvinyl acetate, or non cross-linking ethyl vinyl acetate). In certain embodiments, the adhesive can comprise a carboxylated acrylic, such as a HYCAR®-brand acrylic carboxylated latex (available from B.F. Goodrich Co.).

It should be noted that although most polymers are suitable for use in accordance with the present invention, some polymers may not be suitable when used in combination with particular anti-microbial agents. For example, anionic latex adhesives may be ineffective when used in combination with certain anti-microbial agents, such as quaternary ammonium compounds, Triclosan, or silver zeolite, which are discussed in greater detail below. However, such polymers may be completely suitable when used in conjunction with other anti-microbial agents.

In some embodiments of the present invention, the polymer may also be a polymer that becomes cross-linked when dried. A cross-linked polymer can provide increased wet strength to the base web and can aid in controlling the release time of an anti-microbial agent contained within the formulation. For example, in one embodiment, a liquid latex adhesive capable of becoming cross-linked can be utilized within the polymer mixture. In this embodiment, cross-linking the latex adhesive can provide control over the water absorbency of the wiper, which can be used to effectively control the amount of the anti-microbial agent released when the wiper is contacting by a liquid during wiping. Specifically, by reducing the amount of retained liquid after each rinse cycle, the amount of anti-microbial agent released from the wiper after each rinse cycle is also reduced. In one embodiment of the present invention, the cross-linkable adhesive can be styrene butadiene. In an alternative embodiment, the adhesive can comprise a poly(ethylene vinyl acetate) copolymer.

In some embodiments, a cross-linking agent or catalyst can be added to the polymer mixture to aid in cross-linking the polymer. By varying the amount of cross-linking agent or catalyst utilized, the degree of cross-linking can vary, and thus, the control over release of the anti-microbial agent can be further enhanced. For example, in one embodiment, a poly(ethylene vinyl acetate) copolymer can be cross-linked with N-methyl acrylamide groups using an acid catalyst. Suitable acid catalysts include ammonium chloride, citric acid, maleic acid, and Arizidine catalysts. The carboxylated acrylics are one example of cross-linkable adhesives.

In general, it is often useful to add various other additives to the polymer mixture to modulate the mass transfer rate of the anti-microbial agent and, thereby, the release rate of the anti-microbial agent. For example, a polymer-mixture of the present invention can also contain plasticizers to enhance the migration of the anti-microbial agent to the polymer surface such that it can be more easily removed when the wiper is wetted during use on a surface to be cleaned. One suitable plasticizer includes, for example, glucose triacetate. Moreover, in some embodiments, a polymer mixture of the present can also contain various other components, such as thickeners, defoamers, water, and the like, all of which are well known additives.

Further, other additives, such as composite particles, viscosity modifiers, stabilizers, or surfactants can also be added. Composite particles can generally be added to the polymer mixture to increase the adhesive strength of the polymer mixture without adversely interfering with the other properties of the mixture. Examples of some composite particles that can be used include clay, titanium dioxide, talc, zeolite, silica, or mixtures thereof. Moreover, as stated, one or more stabilizers can be used in the polymer mixture to prevent agglomeration and to increase the stability of the suspension. Stabilizers that may be added to the polymer mixture include cellulose derivatives, such as hydroxy ethyl cellulose or methyl hydroxy cellulose. Other stabilizers that may be used include water-soluble gums, acetates, such as polyvinyl acetate, and acrylics. As stated, the polymer mixture can also contain one or more surfactants. For most applications, nonionic surfactants are preferred.

Besides the above additives, a polymer mixture of the present invention can also include a visual sensor, colorant, or dye to indicate when the anti-microbial agent has been partially or fully exhausted. Some examples of such a visual sensor are provided by the indicator dye described in U.S. Pat. Nos. 3,704,096; 4,205,043; 4,248,597; 4,311,479; 5,317,987; and 5,699,326, all of which are incorporated herein in their entireties by reference thereto. In addition, sodium thiosulfate and various blue dye mechanisms, such as those employed in the previously-mentioned WIPEX® wipes may also be employed. Furthermore, the indicator system disclosed in co-pending U.S. Provisional Application entitled "Use-Dependent Indicator System for Absorbent Articles" may be added to a bonding formulation of the present invention when forming the anti-microbial wiper.

In some applications, it may also be necessary to adjust the pH of the anti-microbial agent and/or the polymer mixture before forming the formulation. In particular, one embodiment of the present invention includes the addition of ammonia to both the polymer mixture and the anti-microbial agent such that the pH of each is adjusted to a more neutral value prior to mixing. The added ammonia generally dissipates during the later step of curing, which is discussed in more detail below.

In general, once the polymer mixture and anti-microbial agent are incorporated into a formulation according to the present invention, the formulation can then be applied to the base web through any known method of application, such as print, print crepe, spraying, blade, saturant, coating, droplet throw, and foam applications. For example, in one embodiment, the formulation can be saturated into the web, such as disclosed in U.S. Pat. No. 5,486,381 to Cleveland et al., which is incorporated herein by reference. Moreover, in another embodiment, the formulation can be printed onto at least one side of the base web, and, in some cases to both outer surfaces of the web. Although any method of application is suitable for use in the present invention, it should be understood that the particular application method utilized can also have an affect on the release rate of the anti-microbial agent. As such, in accordance with the present invention, the method of application can also be selected as desired to further enhance the control over the release time of the anti-microbial agent.

In one embodiment of the present invention, the formulation can be applied to the base web in a pre-selected pattern. For instance, the formulation can be applied to the base web in a reticular pattern, such that the pattern is interconnected forming a net-like design on the surface. Moreover, the formulation can be applied according to a diamond shaped grid. The diamonds, in one embodiment, can be square having a length dimension of ¼ inch. In an alternative embodiment, the diamonds comprising the grid can have length dimensions of 60 mm and 90 mm.

In an alternative embodiment, the formulation can be applied to the base web in a pattern that represents a succession of discrete dots. This particular embodiment is generally well suited for use with lower basis weight wiping products. Applying the formulation in discrete shapes, such as dots, can provide sufficient strength to the base web without covering a substantial portion of the surface area of the web. In particular, applying the formulation to the surface of the base web can, in some instances, adversely affect the absorbency of the web. Thus, in some applications, it may be desired to minimize the amount of formulation applied.

In a further alternative embodiment, the formulation can be applied to the base web according to a reticular pattern in combination with discrete dots. For example, in one embodiment, the formulation can be applied to the base web according to a diamond shaped grid having discrete dots applied to the web within the diamond shapes.

In one embodiment of the present invention, the formulation can also be applied to one or both sides of the base web so as to cover less than 100% of the surface area of the web, particularly from about 10% to about 60% of the surface area of the web. More particularly, in most applications, the formulation will cover from about 20% to about 40% of the surface area of each side of the base web. The total amount of formulation applied to each side of the base web can range from about 2% to about 10% by weight, based upon the total weight of the base web. Thus, when the formulation is applied to each side of the web, the total add-on will be from about 4% to about 20% by weight.

According to one embodiment of the present invention, after the formulation is applied with the base web, one or both of the outer surfaces containing the formulation can then be creped by known creping processes. Although not required, creping at least one side of the base web may sufficiently disrupt the fibers within the web to increase softness, absorbency, and the bulk of the web.

In one embodiment of the present invention, the base web is first pressed into contact with a creping drum by a press roll. The formulation containing the anti-microbial agent that has already been applied to the base web causes only those portions of the web where it has been disposed to adhere to the creping surface. If desired, the creping drum can be heated for promoting attachment between the base web and the surface of the drum, as well as partially drying the base web.

Once adhered to a creping drum, the base web may then be brought into contact with a creping blade that can remove the base web from the creping drum, thereby performing a first controlled pattern crepe on the base web. In applications where the formulation is applied to each side of the base web, the web can also be creped on the second side of the web. In these applications, a second creping blade can perform a second controlled creping operation on the second side of the base web.

In one embodiment of the present invention, after the base web has been applied with the formulation and creped, if desired, the base web may then be dried and cured to form a sufficiently strong anti-microbial wiper. In one embodiment, the base web is pulled through a curing or drying station that can include any form of heating unit, such as an oven energized by infrared heat, microwave energy, hot air or the like. In addition to forming a stronger wiper, the process of curing can also aid in controlling the release time of the anti-microbial agent. Specifically, by altering the degree of polymer curing, the swelling of the polymer mixture in water can be reduced, thereby decreasing the amount of anti-microbial released from the wiper during wiping.

The wipers of the present invention may be used for any use for which a conventional absorbent wiper is used. In particular, the subject wipers are useful as hard-surface wipers where it is desirable for the wiper to have an anti-microbial effect on the surface. An advantage of the subject wipers is that they maintain the ability to provide an anti-microbial solution after they have been rinsed in water multiple times. As mentioned above, in some embodiments, the subject wipers are suitable for use as sanitizers and/or disinfectants.

The present invention may be better understood with reference to the following examples.

General Procedures

Method used in Examples 3–5 for measuring the release of anti-microbial agent from a wiper with multiple washings:

This method provides a simulated rinse cycle (rinse and wring out) for measuring the release of an anti-microbial agent (silver ions in this case) from a treated wiper of the present invention. Five samples were prepared of the treated wiper material (6"×6"@125 grams/m$^2$ (gsm), ShopPro® hand towel). Each sample is weighed dry (as is) and then individually dunked in about 700 ml of moderately hard synthetic fresh water in a 1 liter beaker. Moderately hard synthetic fresh water is 80 parts deionized water, 20 parts PERRIER® water, or equivalent, prepared as described in *Methods For Measuring The Acute Toxicity Of Effluents And Receiving Waters To Freshwater And Marine Organisms*, EPA-600/4-90-027; C. I. Weber, Ed., pp. 32–35; U.S. Environmental Protection Agency, Cincinnati, Ohio (1991). After quickly dunking each individual sample in the water, it is removed and placed horizontally on an foraminous open mesh wire to drain for 10 min. To simulate a wringing or squeezing part of a rinse step, the five samples are placed on top of one another in a clean 6¼ diameter Buchner funnel attached to a vacuum flask and a laboratory vacuum system. The perforated platform of the funnel is covered evenly with the samples and a flexible sheet gasket is positioned on top of the samples to form a vacuum seal to produce a uniform dewatering pressure. The samples are then dewatered using laboratory vacuum for 2 minutes. The samples are then re-weighed to permit the determination of the amount of residual wiper liquid. The fluid extracted from the five samples is collected and tested for silver content (or the content of the anti-microbial agent that is being tested). The content of anti-microbial agent in this liquid is related to the disinfecting strength or ability of the wiper.

After the first rinse and wring cycle, the samples are again individually dunked in the water solution and the steps described above are repeated. The amount of anti-microbial agent can be measured in the wash liquid after each simulated wring step. This can be repeated for as many cycles as desired.

EXAMPLE 1

An anti-microbial wiper was formed from a base web as described above. Once the web was formed, an anti-microbial agent and a polymer mixture were mixed into a formulation that could then be printed onto the web. The anti-microbial agent was an AgION™ silver-zeolite anti-microbial particle obtained from AgION™ Technologies L.L.C, West Hartford, Conn. The polymer mixture included HYCAR RLP resin (available from B.F. Goodrich Specialty Chemicals, Cleveland, Ohio; XAMA-7 (a curing agent available from Sybron Chemicals Inc., Birmingham, N.J.), CMC (as a viscosity modifier, available from Dow Chemical Co., Midland, Mich.), and water. The polymer mixture and anti-microbial agent were incorporated into the formulation such that the anti-microbial agent constituted 1% add-on of the wiper weight. After mixing, the formulation was then printed onto the web in accordance with the present invention.

Once applied with the formulation, the wiper was then tested to determine the amount of silver present in solution after 1, 5, 10, 15, and 20 rinses. Using atomic spectrometer measurements, it was determined that silver remained present at 140 parts per billion (ppb), 100 ppb, 90 ppb, 70 ppb, and 17 ppb, for each respective rinse.

EXAMPLE 2

The ability of an anti-microbial wiper of the present invention to effectively sustain multiple washings was demonstrated. Initially, eight wiper samples (A–H) were formed from a base web as described above. Once the web was formed, a formulation containing AgION™ silver zeolite and a polymer mixture was applied to the web. Samples A–F were applied with the formulation using either print and/or print crepe application methods, while samples G & H were applied with the formulation using a fiber saturation application method, such as described in U.S. Pat. No. 5,486,381 to Cleveland et al. Samples G&H contained approximately 1% silver zeolite. In addition, the characteristics of samples A–F are given below in Table 1:

TABLE 1

Characteristics of samples A–F.

| Sample | Description | % Silver Zeolite | % Binder Solids | % Silver, dry wt. | Creping Tension |
|---|---|---|---|---|---|
| A | Air Product's LTC EVA YAY99A-973 | 1.0 | 37.90 | 0.050 | 110 |
| B | Hycar 76208, 10% PEG (PRINT ONLY) | 0.98 | 37.60 | 0.047 | 0 |
| C | Hycar 2670, 10% PEG4 (PRINT ONLY) | 1.85 | 35.90 | 0.093 | 115 |
| D | Hycar 26706, 8% PEG 450 | 1.85 | 35.90 | 0.093 | 115 |
| E | Hycar 26706, 10% PEG 600 | 0.98 | 37.60 | 0.047 | 105 |
| F | Hycar 26706 | 1.1 | 35.10 | 0.055 | 92 |

To test the samples, each wiper sample was contacted with water for a period of ten (10) minutes. Thereafter, the samples were wrung and allowed to drip such that fluid from the wipers could be collected. The collected fluid was then tested for silver content. After collecting a fluid sample from one washing, various other washings were then conducted. In particular, each sample was washed 20 times, with fluid samples being collected after 1, 5, 10, 15, and 20 washings as described above. The silver content remaining in each sample after 20 washing steps is given in Tables 2–9 below:

TABLE 2

Silver content of fluid collected (Sample A)

| #of Washings | Silver Content (parts per billion) |
|---|---|
| 1 | 210 |
| 5 | 99 |
| 10 | 70 |
| 15 | 270 |
| 20 | 81 |

TABLE 3

Silver content of fluid collected (Sample B)

| #of Washings | Silver Content (parts per billion) |
|---|---|
| 1 | 140 |
| 5 | 67 |
| 10 | 41 |
| 15 | 31 |
| 20 | 18 |

TABLE 4

Silver content of fluid collected (Sample C)

| #of Washings | Silver Content (parts per billion) |
|---|---|
| 1 | 140 |
| 5 | 130 |
| 10 | 46 |
| 15 | 37 |
| 20 | 29 |

TABLE 5

Silver content of fluid collected (Sample D)

| #of Washings | Silver Content (parts per billion) |
|---|---|
| 1 | 110 |
| 5 | 39 |
| 10 | 36 |
| 15 | 26 |
| 20 | 16 |

TABLE 6

Silver content of fluid collected (Sample F)

| #of Washings | Silver Content (parts per billion) |
|---|---|
| 1 | 63 |
| 5 | 180 |
| 10 | 120 |
| 15 | 100 |
| 20 | 57 |

TABLE 7

Silver content of fluid collected (Sample F)

| #of Washings | Silver Content (parts per billion) |
|---|---|
| 1 | 73 |
| 5 | 83 |
| 10 | 14 |
| 15 | <10 |
| 20 | <10 |

TABLE 8

Silver content of fluid collected (Sample G)

| #of Washings | Silver Content (parts per billion) |
|---|---|
| 1 | 180 |
| 5 | 100 |
| 10 | <10 |
| 15 | <10 |
| 20 | <10 |

TABLE 9

Silver content of fluid collected (Sample H)

| #of Washings | Silver Content (parts per billion) |
|---|---|
| 1 | 150 |
| 5 | 75 |
| 10 | <10 |
| 15 | <10 |
| 20 | <10 |

As indicated from Tables 2–9, an anti-microbial wiper of the present invention can controllably release an anti-microbial agent into solution, even after multiple rinsings. It should be understood, however, that a wiper of the present invention can also release an anti-microbial agent after more than 20 washings, as well as over a longer period of time.

Moreover, even after 20 washing steps, an anti-microbial wiper of the present invention can continue to release a sufficient amount of anti-microbial agent to effectively kill microbes. Specifically, according to most literature, a silver content of 20 parts per billion (ppb) can effectively kill microbes, such as *E. Coli* and *Salmonella* spp. As shown in Tables 3–10, samples of the present invention can release sufficient amounts of silver over a period of time to kill such microbes. In fact, through testing, it was determined that each sample tested above had a 99.99% kill efficacy when contacted with *E. Coli* and *Salmonella* spp. for a period of 24 hours, which is the standard exposure time set forth by the EPA.

EXAMPLE 3

This example illustrates the effect of the amount of the anti-microbial formulation and the amount of polymer binder used in the formulation on the silver content in the liquid extracted from the wiper after multiple rinses cycles.

Samples of ShopPro® hand towels (125 gsm basis weight) were treated with AgION™ silver zeolite with the use of HYCAR® #26410 Reactive Liquid Polymer resin as a polymer binder. The towels were treated by the saturation method described above in Examples 1 and 2. Three sets of towels were used and each set was treated with the amounts of silver zeolite and binder resin shown below in Table 10. After treatment, the three sets of towels were subjected to multiple rinse cycles and tested for extract silver concentration as described in the General Procedures.

TABLE 10

Extracted silver ion concentration after multiple rinses as a function of the initial amount of anti-microbial (AgION ™), and release controlling agent (HYCAR #26410) in wipers (ShopPro ®, 125 gsm) treated by saturation.

| SAMPLE DESCRIPTION | NUMBER OF WASHES | SILVER CONCENTRATION IN EXTRACT (ppb) |
|---|---|---|
| CONTROL; 0% AgION ™; 1% HYCAR ® | 1x | <10 |
| | 5x | <10 |
| | 10x | <10 |
| | 15x | <10 |
| | 20x | <10 |
| 1% AgION ™ 1% HYCAR ® | 1x | 140 |
| | 5x | 63 |
| | 10x | 29 |
| | 15x | 14 |
| | 20x | 17 |
| 3% AgION ™ 1% HYCAR ® | 1x | 643 |
| | 5x | 205 |
| | 10x | 96 |
| | 15x | 75 |
| | 20x | 38 |

The data of Table 10 show that the anti-microbial formulation comprising AgION™ silver zeolite and HYCAR® resin binder provided anti-microbial solutions containing silver ions after multiple rinse cycles—at least 20 cycles, in fact. Moreover, the data showed that the level of silver ions in the retained liquid could be controlled by controlling the amount of anti-microbial agent that was initially added to the wipers.

A further set of ShopPro® towels was treated with 1% by weight AgION™ AND 0.5% by weight HYCAR® and tested for the provision of silver in the extract as described above. Here, however, the rinsing cycles were continued to 50 cycles.

TABLE 11

Extract silver ion concentration after multiple rinses in a wiper treated with AgION ™, and HYCAR #26410 in wipers (ShopPro ®, 125 gsm) treated by saturation.

| SAMPLE DESCRIPTION | NUMBER OF WASHES | SILVER CONCENTRATION IN EXTRACT (ppb) |
|---|---|---|
| 1% AgION ™ 0.5% HYCAR ® | 1x | 95 |
| | 5x | 39 |
| | 10x | 26 |
| | 20x | 18 |
| | 30x | 28 |
| | 40X | 15 |
| | 50X | 10 |

A wiper that was treated in the same manner as described for Table 11, was used to measure the time required for the residual liquid retained in the wiper after a rinse cycle to acquire sufficient silver ions in order to become an effective anti-microbial solution. The same technique was used for the test as described in the General Procedures, except that all samples were taken after the fifth rinse cycle, and were taken at the times noted in Table 12.

TABLE 12

Rate of silver release into residual wiper fluid in AgION ™/HYCAR ® treated ShopPro fabric after five rinses.

| SAMPLE DESCRIPTION | RECOVERY TIME (Min. after 5th rinse) | SILVER CONCENTRATION IN EXTRACT (ppb) |
|---|---|---|
| 1% AgION ™ | 0.5 | 36 |
| 0.5% HYCAR ® | 1 | 31 |
|  | 2 | 38 |
|  | 3 | 37 |

As the data shows, the content of the anti-microbial agent in the residual wiper fluid is quickly replenished to a level sufficient for the fluid to act as an effective disinfecting solution. In fact, such replenishment apparently occurs within the first 30 seconds after the sample is squeezed. This indicates that in normal use, the wiper would be capable of supplying an anti-microbial solution very quickly after rinsing.

EXAMPLE 4

In this example, the effect of print treatment as compared with saturant treatment in the preparation of the subject wipers was determined as a function of the ability to continue to provide silver ions in the extract liquid after multiple rinse cycles.

ShopPro® wipers were treated with the anti-microbial formulations as described in Table 13, by either the printing method of applying the formulation, or the saturant method—as both are described in Examples 1 and 2, above. The same amount of anti-microbial formulation (and anti-microbial agent) was used in each case. Table 13 shows the effect of the method of applying the formulation on the amount of silver that is available in the liquid extract after multiple washes.

TABLE 13

Extracted silver concentration after multiple rinses as a function of the method of attachment of anti-microbial agent (AgION ™), and release controlling agent (HYCAR ® #26410) in wipers (ShopPro ® 125 gsm).

| SAMPLE DESCRIPTION | NUMBER OF RINSES[b] | SILVER CONTENT OF EXTRACT (ppb)[a] |
|---|---|---|
| SATURANT TREATED |  |  |
| 1% AgION ™ | 1x | 105 |
| 0.5% HYCAR ® | 5x | 63 |
|  | 10x | 30 |
|  | 20x | 26 |
| PRINT TREATED |  |  |
| 1% AgION ™ | 1x | 250 |
| 0.5% HYCAR ™ | 5x | 90 |
|  | 10x | 89 |
|  | 20x | 86 |

Notes:
[a]Aluminum content on all samples was relatively constant at <50 ppb.
[b]Each rinse comprised a rinse and wring cycle as described above.

As shown in Table 13, both saturate and print treated methods of application of the anti-microbial formulation can be used to produce a product that provides continued release of anti-microbial agent at useful levels even after numerous rinses. With the same formulation, it appeared that the printing method may deliver a higher sustained level of anti-microbial agent over an extended period as compared with the saturant method. Both methods can substantially anchor the anti-microbial agent in the AgION™ formulation to the nonwoven web without significant loss of AgION™ particles during the rinse cycles. This was determined by finding that the content of released aluminum (Al is a component of the zeolite of the AgION™ formulation) in the extract did not substantially vary.

EXAMPLE 5

In this example, the effect of print treatment was compared with saturant treatment on the ability of the wiper to kill test pathogens on the wiper and in the liquid extract after multiple rinse cycles was determined.

ShopPro® wipers were treated with the anti-microbial formulations as described in Tables 14 and 15, by either the printing method of applying the formulation, or the saturant method—as both are described in Examples 1 and 2, above. Tables 14(a) and 14(b) show the effect of the saturant method of applying the formulation on reduction of test pathogens on the wiper fabric and in the liquid extract obtained after a rinse cycle, respectively.

TABLE 14 (a)

Anti-microbial efficacy of wiper liquid extracted from AgION ™/HYGAR ® saturant treated nonwoven fabric wipers[b] after 1,10 and 20 rinse cycles.

| NO. OF RINSE CYCLES | LIVING ORGANISMS AFTER ZERO CONTACT TIME[a] (cfu/ml) | | LIVING ORGANISIMS AFTER 24-HOUR CONTACT TIME (cfu/ml) | | PERCENT REDUCTION % | |
|---|---|---|---|---|---|---|
|  | E. coli | S. choleraesuis | E. coli | S. choleraesuis | E. coli | S. choleraesuis |
| 1x | 2.5 × 10⁵ | 1.9 × 10⁵ | <10 | <10 | 99.99 | 99.99 |
| 10x | 2.6 × 10⁵ | 2.1 × 10⁵ | <10 | <10 | 99.99 | 99.99 |
| 20x | 2.3 × 10⁵ | 2.3 × 10⁵ | <10 | <10 | 99.99 | 99.99 |

Notes:
[a]The efficacy of the treatments was measured according to NAMSA Protocol for Assessment of Antibacterial Finishes on Textile Materials, Antimicrobial Special, Lab No. 99G 09342 00, MSMSA, NAMSA, Northwoods, OH. The anti-microbial strength of the extracts was measured by AATCC Test Method 100 using challenge organisms of *Escherichia coli* (ATCC 43895) and *Salmonella choleraesuis* (ATCC 10708).
[b]ShopPro 125 gsm nonwoven wipers were treated by saturant method with 1% AgION ™ and 0.5% HYCAR ®.

TABLE 14 (b)

Anti-microbial efficacy of wiper fabric AgION ™/HYGAR ® saturant treated nonwoven fabric wipers[b] after 1,10 and 20 rinse cycles.

| NO. OF RINSE CYCLES | LIVING ORGANISMS AFTER ZERO CONTACT TIME[a] (cfu/ml) | | LIVING ORGANISIMS AFTER 24-HOUR CONTACT TIME (cfu/ml) | | PERCENT REDUCTION % | |
|---|---|---|---|---|---|---|
|  | E. coli | S. choleraesuis | E. coli | S. choleraesuis | E. coli | S. choleraesuis |
| 1x | 1.6 × 10⁵ | 1.3 × 10⁵ | 5.5 × 10² | 4.6 × 10³ | 99.66 | 96.17 |
| 5x | 1.5 × 10⁵ | 1.2 × 10⁵ | 1.0 × 10² | 1.8 × 10⁵ | 99.94 | NR |
| 10x | 1.5 × 10⁵ | 1.1 × 10⁵ | 6.0 × 10² | 8.0 × 10² | 99.61 | 99.27 |
| 20x | 1.6 × 10⁵ | 9.4 × 10⁴ | <1.0 × 10² | <1.0 × 10² | 99.94 | 99.90 |

Notes:
[a]The efficacy of the treatments was measured according to NAMSA Protocol for Assessment of Antibacterial Finishes on Textile Materials, Antimicrobial Special, Lab No. 99G 09342 00, MSMSA, NAMSA, Northwoods, OH. The anti-microbial strength of the extracts was measured by AATCC Test Method 100 (modified) using challenge organisms of *Escherichia coli* (ATCC 43895) and *Salmonella choleraesuis* (ATCC 10708).
[b]ShopPro 125 gsm nonwoven wipers were treated by saturant method with 1% AgION ™ and 0.5% HYCAR ®.

Tables 15(a) and 15(b) show the effect of the printing method of applying the formulation on reduction of test pathogens on the wiper fabric and in the liquid extract obtained after a rinse cycle, respectively.

TABLE 15 (a)

Anti-microbial efficacy of wiper liquid extracted from AgION ™/HYGAR ® printing treated nonwoven fabricc wipers[b] after 1,10 and 20 rinse cycles.

| NO. OF RINSE CYCLES | LIVING ORGANISMS AFTER ZERO CONTACT TIME[a] (cfu/ml) | | LIVING ORGANISIMS AFTER 24-HOUR CONTACT TIME (cfu/ml) | | PERCENT REDUCTION % | |
|---|---|---|---|---|---|---|
| | E. coli | S. choleraesuis | E. coli | S. choleraesuis | E. coli | S. choleraesuis |
| 1x | 2.2 × 105 | 1.3 × 105 | <10 | <10 | 99.99 | 99.99 |
| 10x | 2.9 × 105 | 1.1 × 105 | <10 | <10 | 99.99 | 99.99 |
| 20x | 2.0 × 105 | 1.3 × 105 | <10 | <10 | 99.99 | 99.99 |

Notes:
[a]The efficacy of the treatments was measured according to NAMSA Protocol for Assessment of Antibacterial Finishes on Textile Materials, Antimicrobial Special, Lab No. 99G 09342 00, MSMSA, NAMSA, Northwoods, OH. The anti-microbial strength of the extracts was measured by AATCC Test Method 100 using challenge organisms of *Escherichia coli* (ATCC 43895) and *Salmonella choleraesuis* (ATCC 10708).
[b]ShopPro 125 gsm nonwoven wipers were treated by printing method with 1% AgION ™ and 0.5% HYCAR ®.

TABLE 15 (b)

Anti-microbial efficacy of wiper fabric AgION ™/HYGAR ® printing treated nonwoven fabric wipers[b] after 1,10 and 20 rinse cycles.

| NO. OF RINSE CYCLES | LIVING ORGANISMS AFTER ZERO CONTACT TIME[a] (cfu/ml) | | LIVING ORGANISIMS AFTER 24-HOUR CONTACT TIME (cfu/ml) | | PERCENT REDUCTION % | |
|---|---|---|---|---|---|---|
| | E. coli | S. choleraesuis | E. coli | S. choleraesuis | E. coli | S. choleraesuis |
| 1x | 1.3 × 105 | 1.6 × 105 | <1.0 × 102 | 3.0 × 102 | 99.93 | 99.83 |
| 5x | 1.4 × 105 | 1.9 × 105 | 1.0 × 102 | <1.0 × 102 | 99.93 | 99.95 |
| 10x | 1.3 × 105 | 1.6 × 105 | 1.0 × 102 | 1.0 × 103 | 99.93 | 99.86 |
| 20x | 1.5 × 105 | 1.7 × 105 | <1.0 × 102 | <1.0 × 102 | 99.93 | 99.94 |

Notes:
[a]The efficacy of the treatments was measured according to NAMSA Protocol for Assessment of Antibacterial Finishes on Textile Materials, Antimicrobial Special, Lab No. 99G 09342 00, MSMSA, NAMSA, Northwoods, OH. The anti-microbial strength of the extracts was measured by AATCC Test Method 100 (modified) using challenge organisms of *Escherichia coli* (ATCC 43895) and *Salmonella choleraesuis* (ATCC 10708).
[b]ShopPro 125 gsm nonwoven wipers were treated by printing method with 1% AgION ™ and 0.5% HYCAR ®.

It was shown that either the saturant treated or the printing treated wipers provided liquid extract after 20 rinse cycles that was capable of obtaining a 99.99% kill on both *E. coli* and *S. choleraesuis* test pathogens. Accordingly, it is believed that either of these methods is capable of providing effective anti-microbial wipers of the present invention.

In the measurements of the retardation of cell growth on the wiper fabric itself, neither method of treatment provided as complete a reduction as did the liquid effluents—although a reduction of at least 99% was obtained in most cases. It is possible that this indicates a less effective contact of the wiper surface (and the anti-microbial agent) with the microorganisms that were applied to the surface. This could indicate that the surface of the wiper could be less irritating to the skin of the user when more aggressive anti-microbial agents are employed.

EXAMPLE 6

Another exemplary wiper product was produced by flexogravure printing a Hydroknit® material (125 gsm) with a blue ink having an overall shell pattern to provide a total AgION™ add-on of 0.20% (based on weight of the AgION™ anti-microbial per weight of wiper material). The ink consisted of a mixture of cross-linkable acrylic, AgION™ silver-zeolite complex, blue pigment (Graphtol 6825, available from Clariant), and various ink modifiers as set forth below:

TABLE 16

Exemplary Anti-Microbial Wiper Formulation

| COMPONENT | % ACTIVE | % AMOUNT BY WEIGHT |
|---|---|---|
| Hydroknit ® (125 gsm) | | |
| AgION ™ anti-microbial silver zeolite complex | 20 | 48.6 |
| Hycar 26684 | 50 | 19.4 |
| Xama-7 | 100 | 0.3 |
| Graphtol 6825 | 20 | 1.4 |
| Ammonium hydroxide | 27 | 1.0 |
| Water | | 29.3 |

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed is:

1. A method of forming an anti-microbial wiper capable of providing a liquid anti-microbial solution after multiple rinse cycles, the method comprising the steps of:
   providing a controlled release anti-microbial formulation comprising an anti-microbial agent and a polymer selected from the group consisting of acrylate polymers, styrene butadiene polymers, vinyl chloride polymers, methacrylate polymers, acrylic polymers, vinyl acetate polymers, and mixtures thereof, wherein said polymer is cross-linkable;
   adhering said formulation to an absorbent web containing fibers; and
   cross-linking said polymer;
   wherein said web retains liquid after each rinse cycle, and wherein said formulation releases sufficient anti-microbial agent into the retained liquid after each of at least five normal rinse cycles so that the retained liquid is an anti-microbial solution and said retained liquid is capable of disinfecting a hard surface that is wiped with said anti-microbial wiper.

2. A method as defined in claim 1, wherein said cross-linked polymer is capable of swelling upon exposure to water such that the degree of swelling of said cross-linked polymer at least partially controls said release of said anti-microbial agent.

3. A method as defined in claim 2, wherein said polymer is a carboxylated acrylic latex.

4. A method as defined in claim 1, wherein said anti-microbial formulation comprises a source of anti-microbial metal ions.

5. A method as defined in claim 4, wherein said anti-microbial formulation comprises a source of ions of a metal selected from the group consisting of silver, copper, zinc, mercury, antimony, lead, bismuth, cadmium, chromium and thallium.

6. A method as defined in claim 5, wherein said metal comprises silver.

7. A method as defined in claim 1, wherein said anti-microbial formulation comprises a source of free chlorine.

8. A method as defined in claim 1, wherein said anti-microbial formulation comprises calcium hypochlorite particles.

9. A method as defined in claim 1, wherein said anti-microbial formulation comprises a quaternary ammonium compound.

10. A method as defined in claim 9, wherein said quaternary ammonium compound comprises alkyl aryl benzonium chloride.

11. A method as defined in claim 1, wherein said antimicrobial formulation further comprises an additive selected from the group consisting of a cross-linking agent, a catalyst, a thickener, a plasticizer, a defoamer, a colorant, a visual sensor, a pigment, composite particles, a viscosity modifier, a stabilizer, a surfactant, and combinations thereof.

12. A method as defined in claim 1, wherein the adhering of said anti-microbial formulation comprises spraying the formulation onto said web.

13. A method as defined in claim 1, wherein the adhering of said formulation onto said web comprises a process chosen from the group consisting of printing, blade applying, coating, droplet throwing, print creping, saturating, and foam applying.

14. A method as defined in claim 1, wherein said web has at least two surfaces, said formulation being applied to said at least one of said two surfaces of said web in a pre-selected pattern.

15. A method as defined in claim 14, wherein said formulation covers from about 10% to about 60% of said at least one surface of said web.

16. A method as defined in claim 14, wherein said formulation covers from about 20% to about 40% of said at least one surface of said web.

17. A method as defined in claim 14, wherein said formulation covers from about 10% to about 60% of both surfaces of said web.

18. A method as defined in claim 1, wherein said polymer is cross-linked after said formulation has been applied to said web.

19. A method as defined in claim 14, further comprising the step of creping said at least one surface of said web to soften said web after said formulation has been applied to said web.

20. A method as defined in claim 1, wherein said fibers of said web comprise pulp fibers.

21. A method as defined in claim 1, wherein said fibers of said web comprise synthetic fibers.

22. A method of forming an anti-microbial wiper for disinfecting hard surfaces comprising the steps of:
providing a cloth-like absorbent base web containing fibers and capable of retaining liquid after a rinse cycle, said absorbent web having two outer surfaces;

adhering an anti-microbial formulation to said absorbent web, said anti-microbial formulation comprising an anti-microbial agent and a polymer selected from the group consisting of acrylate polymers, styrene butadiene polymers, vinyl chloride polymers, methacrylate polymers, acrylic polymers, vinyl acetate polymers, and mixtures thereof, wherein said polymer is cross-linkable; and cross-linking said polymer;

wherein said anti-microbial agent is capable of activation when said absorbent web is contacted with a liquid, said activation including the release of a portion of said anti-microbial agent into the retained liquid to form an anti-microbial solution, said cross-linked polymer being capable of controlling the rate of release of the anti-microbial agent from the anti-microbial formulation so that said anti-microbial solution is formed after at least five rinse cycles and said retained liquid is capable of disinfecting a hard surface that is wiped with said anti-microbial wiper.

23. A method as defined in claim 22, wherein said antimicrobial formulation further comprises an additive selected from the group consisting of a cross-linking agent, a catalyst, a thickener, a plasticizer, a defoamer, a colorant, a visual sensor, a pigment, composite particles, a viscosity modifier, a stabilizer, a surfactant, and combinations thereof.

24. A wiper capable of providing liquid anti-microbial solution after numerous rinse cycles comprising:
a controlled release anti-microbial formulation comprising an anti-microbial agent and a polymer selected from the group consisting of acrylate polymers, styrene butadiene polymers, vinyl chloride polymers, methacrylate polymers, acrylic polymers, vinyl acetate polymers, and mixtures thereof, wherein said polymer is cross-linked, which formulation is adhered to an absorbent web which retains liquid after each rinse cycle, wherein said formulation releases sufficient anti-microbial agent into the retained liquid after each of at least five normal rinse cycles so that the retained liquid is an anti-microbial solution and said retained liquid is capable of disinfecting a hard surface that is wiped with said anti-microbial wiper.

25. A wiper as defined in claim 24, wherein said polymer comprises a carboxylated acrylic latex.

26. A wiper as defined in claim 24, wherein said anti-microbial agent comprises a source of metal ions where the metal is selected from the group consisting of silver, copper, zinc, mercury, antimony, lead, bismuth, cadmium, chromium and thallium.

27. A wiper as defined in claim 26, wherein said metal comprises silver.

28. A wiper as defined in claim 24, wherein said anti-microbial formulation comprises a source of free chlorine.

29. A wiper as defined in claim 24, wherein said anti-microbial formulation comprises a source of chlorine dioxide.

30. A wiper as defined in claim 24, wherein said anti-microbial formulation comprises calcium hypochlorite particles.

31. A wiper as defined in claim 24, wherein said anti-microbial formulation comprises a quaternary ammonium compound.

32. A wiper as defined in claim 31, wherein said quaternary ammonium compound comprises alkyl aryl benzonium chloride.

33. A wiper s defined in claim 24, wherein said antimicrobial formulation further comprises an additive selected from the group consisting of a cross-linking agent, a catalyst, a thickener, a plasticizer, a defoamer, a colorant, a visual sensor, a pigment, composite particles, a viscosity modifier, a stabilizer, a surfactant, and combinations thereof.

34. A wiper as defined in claim 24, wherein said formulation covers from about 10% to about 60% of said at least one surface of said web.

35. A wiper as defined in claim 24, wherein said formulation covers from about 20% to about 40% of said at least one surface of said web.

36. A wiper as defined in claim 24, wherein said formulation covers from about 10% to about 60% of both surfaces of said web.

37. A wiper as defined in claim 24, wherein said fibers of said web compose pulp fibers.

38. A wiper as defined in claim 24, wherein said fibers of said web comprise synthetic fibers.

* * * * *